US012765831B2

(12) United States Patent
Teplica et al.

(10) Patent No.: US 12,765,831 B2
(45) Date of Patent: Oct. 20, 2026

(54) ANTHROPOMORPHIC CAMERA FOR STANDARDIZED IMAGING AND CREATION OF ACCURATE THREE-DIMENSIONAL BODY SURFACE AVATARS

(71) Applicant: HumanImage Inc, Chicago, IL (US)

(72) Inventors: David Teplica, Chicago, IL (US); Jamey Srock, North Hollywood, CA (US)

(73) Assignee: HumanImage Inc, Chicago, IL (US)

( * ) Notice: Subject to any disclaimer, the term of this patent is extended or adjusted under 35 U.S.C. 154(b) by 431 days.

(21) Appl. No.: 18/217,420

(22) Filed: Jun. 30, 2023

(65) Prior Publication Data

US 2024/0000373 A1 Jan. 4, 2024

Related U.S. Application Data

(60) Provisional application No. 63/358,095, filed on Jul. 1, 2022.

(51) Int. Cl.
*A61B 5/00* (2006.01)
*G06T 15/00* (2011.01)

(52) U.S. Cl.
CPC ............ *A61B 5/441* (2013.01); *A61B 5/0064* (2013.01); *A61B 5/0077* (2013.01); *G06T 15/00* (2013.01)

(58) Field of Classification Search
None
See application file for complete search history.

(56) References Cited

U.S. PATENT DOCUMENTS

| | | | | |
|---|---|---|---|---|
| 2009/0118600 A1* | 5/2009 | Ortiz | A61B 5/0064 | 600/306 |
| 2010/0232773 A1* | 9/2010 | DePaula | A61B 5/6888 | 396/5 |
| 2012/0206587 A1* | 8/2012 | Oz | A61B 5/444 | 348/E7.085 |
| 2018/0125370 A1* | 5/2018 | Curiel | A61B 5/702 | |
| 2019/0105842 A1 | 4/2019 | Dau et al. | | |
| 2019/0166312 A1* | 5/2019 | Tashayyod | H04N 23/951 | |

FOREIGN PATENT DOCUMENTS

WO 2018/113885 A1 6/2018

* cited by examiner

*Primary Examiner* — Jason M Sims
*Assistant Examiner* — Matthew Eric Ogles
(74) *Attorney, Agent, or Firm* — Dykema Gossett PLLC

(57) ABSTRACT

A device for standardized and repeatable imaging of a body surface, including a stack of imaging sensors that are each independently moved to a standard imaging distance from the body surface as the stack is rotated about a central axis of the body. Distance sensors are used to determine the required location of each imaging sensor, which is moved independently so that each imaging sensor is at the same distance from an irregular body surface, and the stack matches the shape of the body surface, even as the stack is rotated around the body. The distance between imaging sensors in the stack can be adjusted to match the height of the body. Methods of use are also disclosed.

7 Claims, 6 Drawing Sheets

ANTHROPOMORPHIC CAMERA FOR STANDARDIZED IMAGING AND CREATION OF ACCURATE THREE-DIMENSIONAL BODY SURFACE AVATARS

RELATED APPLICATIONS

This application claims the benefit of U.S. Provisional Application No. 63/358,095, filed on Jul. 1, 2022, entitled "ANTHROPOMORPHIC MEDICAL IMAGING DEVICE TO CREATE EXACT VOLUMETRIC AVATARS OF THE HUMAN BODY WITH FULLY RENDERED SKIN SURFACES USING VISIBLE LIGHT", which application(s) are incorporated herein by reference in their entirety.

FIELD OF THE INVENTION

The invention relates to imaging apparatus and methods for creating images of a three-dimensional object. More specifically, the invention includes a camera for controlled and reproducible imaging of a body. The invention may be used, for example, to create highly standardized images of the skin of a patient with minimal geometric or other distortion. Methods of imaging an object are also provided.

BACKGROUND ART

Several body surface imaging devices have come to market over the last few decades with the goal of improving skin cancer detection, but each creates a semblance of three-dimensional form using data assembled from two or more fixed cameras that capture images with non-standardized parameters, such as varying orientation angles, perspective, focus distance, depth of field, and lighting variations. Each camera is at a different distance from a body surface that is not necessarily standardized meticulously for position relative to the body surface, and with images captured at different focal distances, varying orientation angles and perspective views, and sometimes with different focal length lenses, and with widely differing lighting and exposure values. These non-standardized images are manipulated to create an extrapolated three-dimensional form that includes zones between camera harvest angles where computer generated "fill" gives an illusion of three-dimensionality but lacks true surface details.

Another approach has been flatbed scanning of a three-dimensional body; however, scanner imagers typically have a very narrow depth of field, so that any portions of the body that are beyond this short distance from the scanner bed will be out of focus and not useful for accurate analysis or sequential tracking of skin features over time. Hand-held scanners have the same deficiencies, and even greater problems with standardization and registration, and are more dependent on the operator technique, with unreliable results due to operator errors.

Without strict standardization, and with reliance on extrapolation to fill in the skin surface and create volumetric form, these technologies have failed to give clinical value for the detection of skin cancers or finding early changes in skin in a way that improves diagnosis or cure.

BRIEF SUMMARY OF THE INVENTION

The present invention preferably includes a camera having multiple imaging elements in a vertical arrangement that sweeps around a body to obtain standardized images of the surface of the body, with each imaging element automatically positionable at a single specified distance from the surface of the body. In an example embodiment of imaging the skin of a human patient, the patient is located in a central imaging chamber or area, with the imaging elements directed inward towards the patient. In some embodiments, the imaging elements are automatically adjusted in elevation so that all imaging elements can be utilized regardless of a patient's height. In some embodiments, the invention includes 4 sets of imaging elements, each set arranged in a multi-level stack at one of 4 quadrants around the central imaging chamber, with spacing between imaging elements in each stack adjustable so that the stack covers the particular patient's height, and with each imaging element positionable closer to or farther from a central axis of the central imaging chamber so that each imaging element is located a predetermined distance from the skin of the patient.

In one embodiment, a medical imaging device for creating a three-dimensional image of a body surface can comprise a sensor array comprising a plurality of sensors, each sensor comprising a sensor plate, and each sensor configure to collect skin data regarding skin features and conditions. The medical imaging device can further comprise means for adjusting a standoff distance from the body surface to each sensor plate of each sensor in said sensor array, creating an array of standoff distances, wherein each standoff distance comprising said array of standoff distances may be unique from each other standoff distance comprising said array of standoff distances, and whereby said plurality of sensors are adapted to mirror a shape of the body surface, means for adjusting a sensor vertical separation distance between adjacent sensors of said sensor array, means to facilitate movement of said sensors array around the body surface to capture images of the body surface from various angles while maintaining at least one target standoff distance and collecting spatially registered skin data, means for generating a volumetric point cloud representing the body surface; and means for storing said spatially registered skin data tied to said volumetric point cloud.

In another embodiment, an anthropomorphic body surface scanner can comprise a plurality of imaging sensors mounted for relative movement between said plurality of imaging sensors and the body surface. Each can comprise an imaging sensor lens and each imaging sensor in said plurality of imaging sensors is vertically separated from each other imaging sensor in said plurality of imaging sensors. The vertical separation is maintained by a pantographic mechanism. A first plurality of lasers configured to provide input to maintain a predetermined distance between each imaging sensor lens and the body surface, a second plurality of lasers configured to provide input to maintain a desired vertical separation of said imaging sensors in said plurality of imaging sensors; and an image processor for extracting skin data from images captured by said plurality of imaging sensors.

In yet another embodiment, a method of creating a three-dimensional representation of skin features and conditions on a volumetric point cloud representing a human body surface can comprise collecting, at an initial point in time, an initial plurality of highly standardized, three dimensional images of the human body surface comprising a plurality of skin locations, extracting initial diagnostic data from said initial plurality of three-dimensional images, registering said initial diagnostic data to said plurality of skin locations, creating an initial skin map of registered diagnostic data, storing said initial skin map, collecting, at a subsequent point in time, a subsequent plurality of highly standardized, three dimensional images of the human body surface comprising said plurality of skin locations, extracting subsequent diagnostic data from said subsequent plurality of three-dimensional images, registering said subsequent diagnostic data to said plurality of skin locations, creating an subsequent skin map of registered diagnostic data, storing said subsequent skin map, comparing said initial skin map to said subsequent skin map, thereby identifying differential skin data; and identifying for a clinician any abnormal skin conditions based on said differential skin data.

These and various other advantages and features of novelty which characterize the present invention are pointed out with particularity in the claims annexed hereto and forming a part hereof. However, for a better understanding of the invention, its advantages and objects obtained by its use, reference should be made to the drawings which form a further part hereof, and to the accompanying descriptive matter, in which there is illustrated and described preferred embodiments of the present invention.

BRIEF DESCRIPTION OF THE DRAWINGS

In the drawings, in which corresponding reference numerals and letters indicate corresponding parts of the various embodiments throughout the several views, and in which the various embodiments generally differ only in the manner described and/or shown, but otherwise include parts corresponding to the parts in the previously described embodiment.

DETAILED DESCRIPTION OF THE INVENTION

Various embodiments are described herein of various apparatus and/or systems. Numerous specific details are set forth to provide a thorough understanding of the overall structure, function, manufacture, and/or use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," "an exemplary embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," "in an exemplary embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

Figure 1:
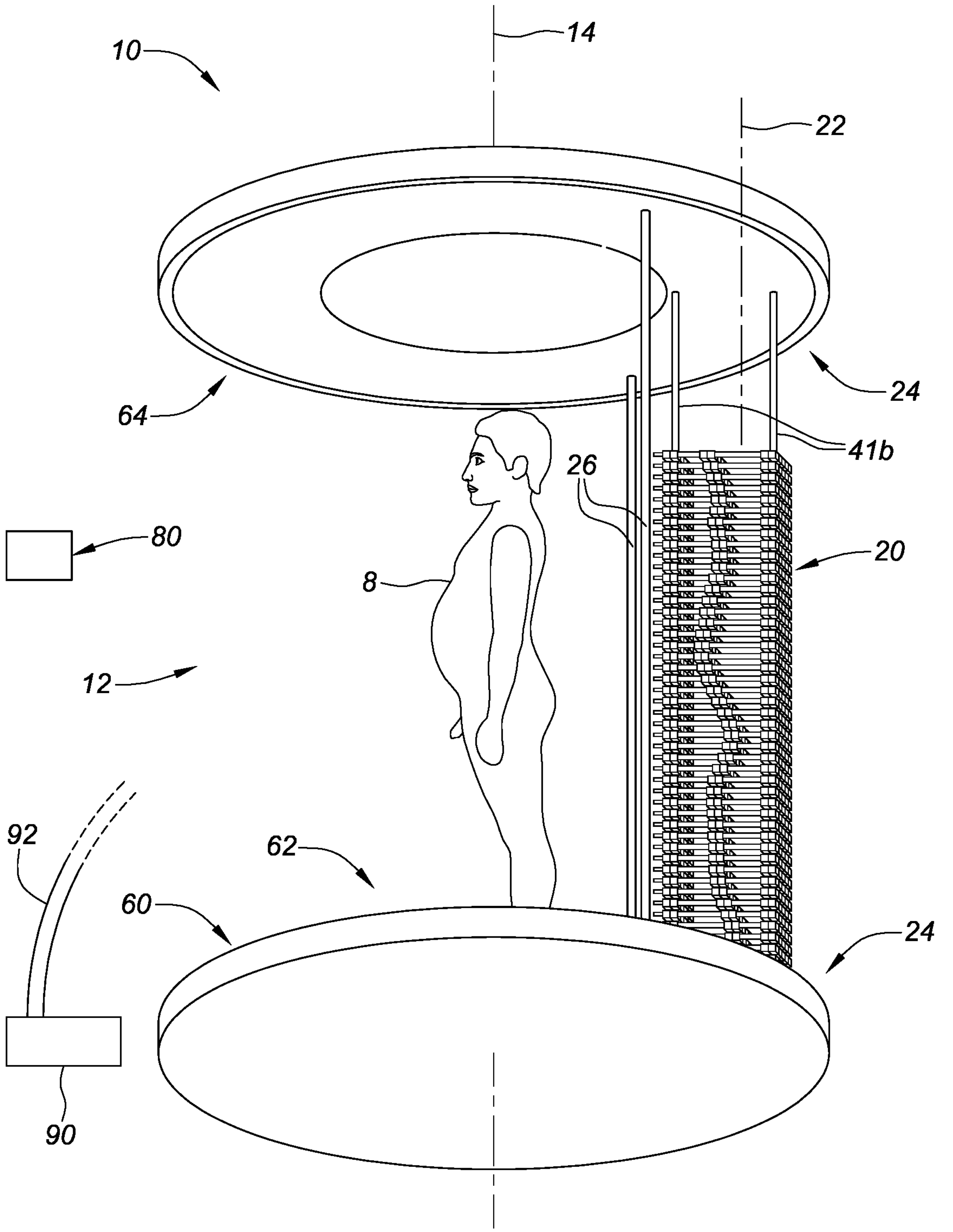
FIG. 1 is a schematic perspective illustration of a camera of the present invention, with a vertical central axis and a target body within an imaging chamber, and a stack of imaging clusters arranged proximate the periphery of the camera.
Figure 3:
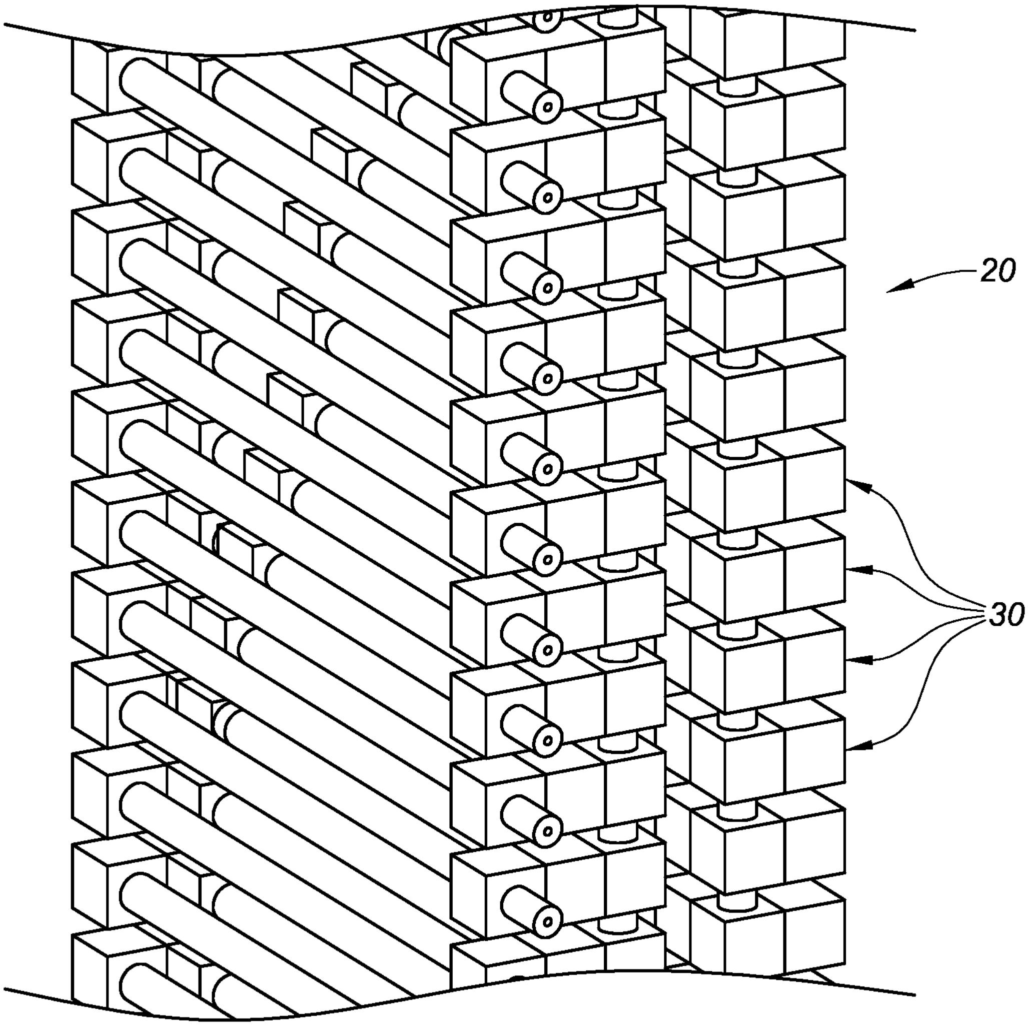
FIG. 3 is a schematic perspective illustration of a stack of imaging clusters of the camera of FIG. 1, shown with pantograph arms removed to show underlying structure indicating varied standoff distances among imaging sensors.

Referring now to the drawings, the invention preferably includes an imaging device or camera 10 having a plurality of imaging sensors 50 arranged near the periphery of the camera 10 and having an interior space or imaging chamber 12 in which a three-dimensional body, human patient, or other body 8 to be imaged is positioned in various embodiments. For example, the body 8 can be a human patient positioned within the interior space 12, and the imaging sensors 50 are arranged and oriented to obtain image data or images 80 of the skin of the patient 8. The images 50 of the skin can be useful for a variety of medical diagnostic or other purposes, including documentation or evaluation of skin lesions. Further, when the camera 10 is used to create standardized images over time, any changes in the body 8, such as development or changes of a skin lesion, can be monitored and documented. In one embodiment, the camera 10 can includes at least one array or stack 20 of imaging clusters 30 arranged in a generally vertical array along a stack axis 22, with each of the imaging clusters 30 comprising a standoff distance sensor 36, an imaging sensor 50, attached pantograph arms 41*e*, and a standoff positioning mechanism 38. In other embodiments, the camera can comprise a subset of these components as may be needed for particular tasks and imaging output. A camera 10 of the present invention is illustrated schematically in a perspective view in FIG. 1, which shows a patient body 8 within the imaging chamber 12, standardized for position at the central axis 14, with a stack 20 of imaging clusters 30 aligned by vertical sensor-separation glide bars or spacing alignment guides 41*b* that are secured to the upper turntable 64 and lower turntable 60, that rotate by action of a stack rotation mechanism 24 around the central platform 62 on which the patient is standing. A portion of the stack 20 is schematically further illustrated in perspective view in FIG. 3, which illustrates a number of imaging clusters 30 in the stack 20. In other embodiments, the body can rotate on a turntable while the stack is static.

Figure 2:
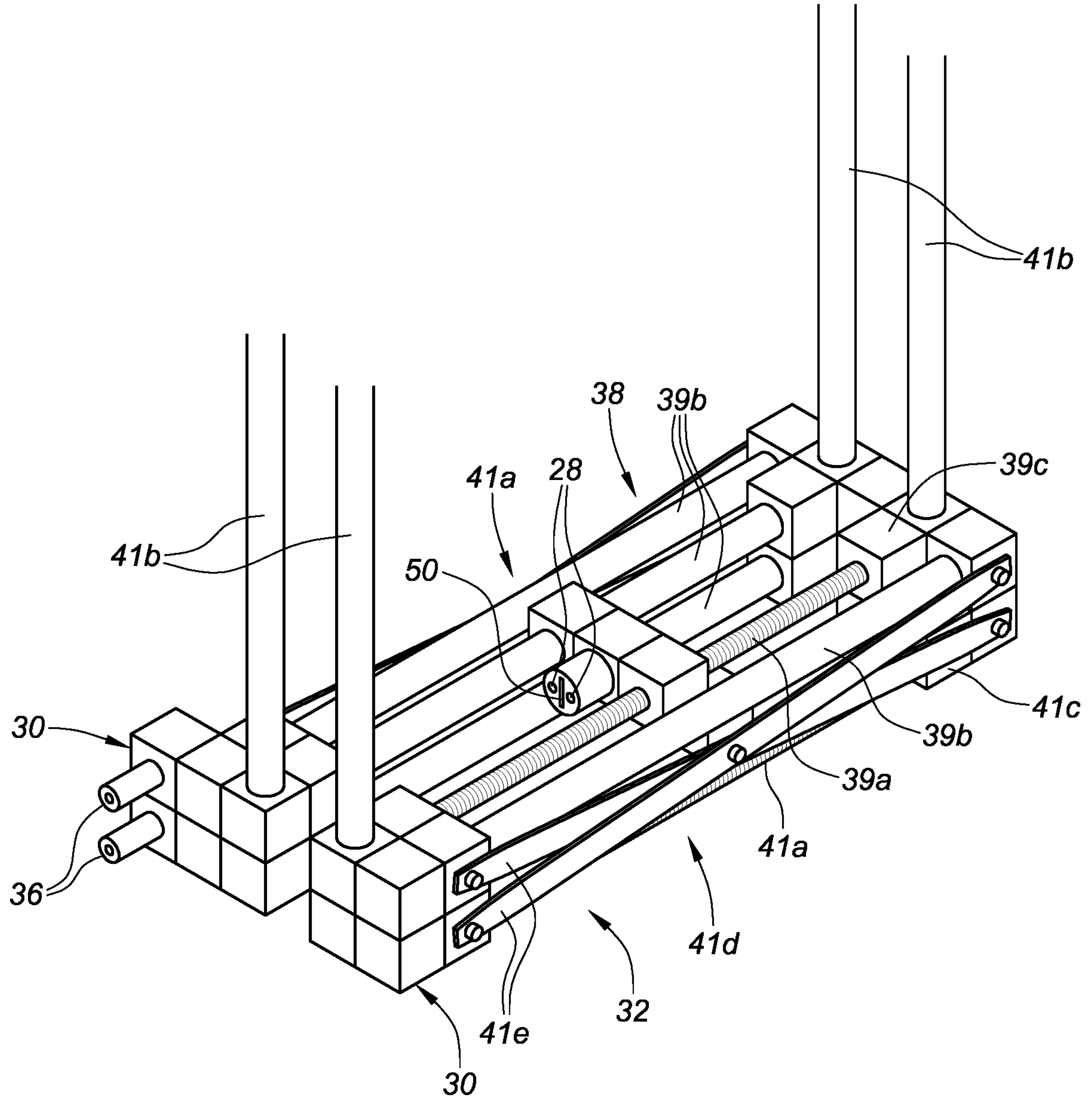
FIG. 2 is a schematic perspective illustration of an imaging cluster of the camera of FIG. 1, with an imaging sensor, a standoff positioning mechanism, and a cluster spacing mechanism.

The stack 20 of imaging clusters 30 can comprise a plurality of lighting elements 26, 28 for illuminating the body 8 in a controlled manner. In one embodiment, the lighting elements 26 comprise an opposed pair of LED strip lights aligned parallel to the stack axis 22 and positioned on both sides of the imaging stack 20 at about a 45-degree angle with respect to the central axis 14 to provide consistent ambient or fill-lighting and minimize variable shadowing. In another embodiment, the lighting elements can comprise a plurality of discrete lighting elements. In one embodiment, the lighting elements 26 are arranged so that the lighting elements 26 rotate with the stack 20 as the stack 20 rotates around the body 8 to capture images as described herein. In another embodiment, the lighting elements can be static as the stack rotates around the body or the body rotates in relation to the stack to capture images as described herein. The imaging clusters 30 include lighting elements 28 located on each side of the imaging sensor 50 to produce controlled lighting at each respective imaging cluster 30. The lighting elements 28 can comprise point sources of light such as LED elements, although LED ring lights or other lights located around each respective imaging sensor 50 can be utilized. One embodiment of two imaging clusters 30 is schematically illustrated in a perspective view in FIG. 2, which shows two imaging clusters 30, each having two lighting elements 28, a standoff distance sensor 36, a standoff positioning mechanism 38, a standoff linear motion screw 39*a*, horizontal sensor glide bars or standoff alignment guides 39*b*, a standoff drive motor 39*c*, and attached pantograph arms 41*e*.

The camera 10 can include means for controlling the lighting elements 26, 28 to achieve a standardized lighting of the surface of the body 8, such as by adjusting the intensity of the lighting elements 26, 28, or selectively illuminating only some of the lighting elements 26, 28, or by adjusting the color temperature of the lighting elements 26, 28, for example. In some embodiments, the lighting elements 26, 28 can produce electromagnetic radiation in the form of visible light, such as a neutral or white light, or light of one or more specific wavelengths. In some embodiments, the lighting elements 26, 28 can produce non-visible wavelengths, such as infrared or ultraviolet radiation. In some embodiments, the lighting elements 26, 28 can produce a electromagnetic radiation in a combination of visible and non-visible wavelengths. In some embodiments, the lighting elements 26, 28 can emit various wavelengths, and the means for controlling the lighting elements 26, 28 can adjust the wavelengths or specific lighting elements 26, 28 or selectively illuminate only some of the lighting elements 26, 28 that emit specific wavelengths.

In one embodiment, the stack 20 can include at least one height detector 40 that detects the height or extent 9 of the body 8 along the central axis 14. The height detector 40 can include an infrared sensor, although optical, ultrasonic, laser, LIDAR, or other sensors can be utilized alternatively or in combination with an infrared sensor. In some embodiments, a single height detector 40 can be utilized, and moved parallel to the stack axis to determine a body height 9 of the body 8 to be imaged. In other embodiments, one or more of the imaging clusters 30 can each incorporate a height detector 40 to detect whether the body 8 extends to the imaging view of the respective imaging sensor 50. Also illustrated in the example shown in FIG. 2, the cluster spacing mechanism 32 includes vertical spacing alignment guides 41*b*, a spacing drive motor 41*c* that rotates a spacing linear motion screw 41*a*, and the imaging clusters 30 are coupled by a spacing pantograph mechanism 41*d* including a plurality of pantograph arms 41*e*. In other embodiments, the height of the imaging clusters can be manually adjusted. In some embodiments, the spacing between the imaging clusters 30 can be independently controlled, so that the spacing between some of the imaging clusters 30 can be adjusted to be different from the spacing between other of the imaging clusters 30; in these embodiments, a single spacing pantograph mechanism 41*d* secured to all imaging clusters 30 in the stack 20 is not used, but the cluster spacing mechanism 32 can include a plurality of spacing pantograph mechanisms 41*d*, each of the plurality of spacing pantograph mechanisms 41*d* being secured to less than all imaging clusters 30 in the stack 20. In some embodiments, alternative cluster spacing mechanisms 32 can be utilized, such as spacing linear motion screws 41*a* incorporated into a plurality of imaging clusters 30, with corresponding spacing drive motors 41*c*, to adjust spacing between adjacent imaging clusters 30. In some embodiments, spacing between certain adjacent imaging clusters 30 can be chosen to provide more detailed imaging information for some portions of the body 8 that closer examination is desired, such as portions of the body 8 that have previously-identified skin anomalies, compared to other portions of the body 8 that are being imaged for screening purposes, for example.

The standoff distance sensor 36 is oriented to sense the distance between the standoff distance sensor 36 and the particular portion of the body 8 that is imaged by the particular imaging sensor 50. The standoff distance sensor 36 can comprise an infrared distance sensor, although optical, ultrasonic, laser, LIDAR or other distance sensors can be utilized to adjust the standoff positioning mechanism 38 so that the imaging sensor 50 is a predetermined standoff distance 70 from the respective portion of the body 8 being imaged by the respective imaging sensor. The standoff positioning mechanism 38 can comprise a standoff linear motion screw 39*a* that is rotated by standoff drive motor 39*c* to drive the imaging sensor 50 closer to the body 8 or farther from the body 8 as needed to maintain the imaging sensor 50 at the predetermined standoff distance 70 from the body 8. The imaging sensor 50 can be coupled to the standoff linear motion screw 39*a* and follows along a standoff alignment guide 39*b* to maintain orientation of the imaging sensor 50 directed to the particular portion of the body 8 being imaged by the respective image sensor. The standoff linear motion screw 39*a* can comprise a ball screw, although a lead screw, Acme screw, roller screw, threaded rod, or other linear actuator arrangements can be utilized to move the imaging sensor 50 to maintain the predetermined standoff distance 70.

Figure 4A:
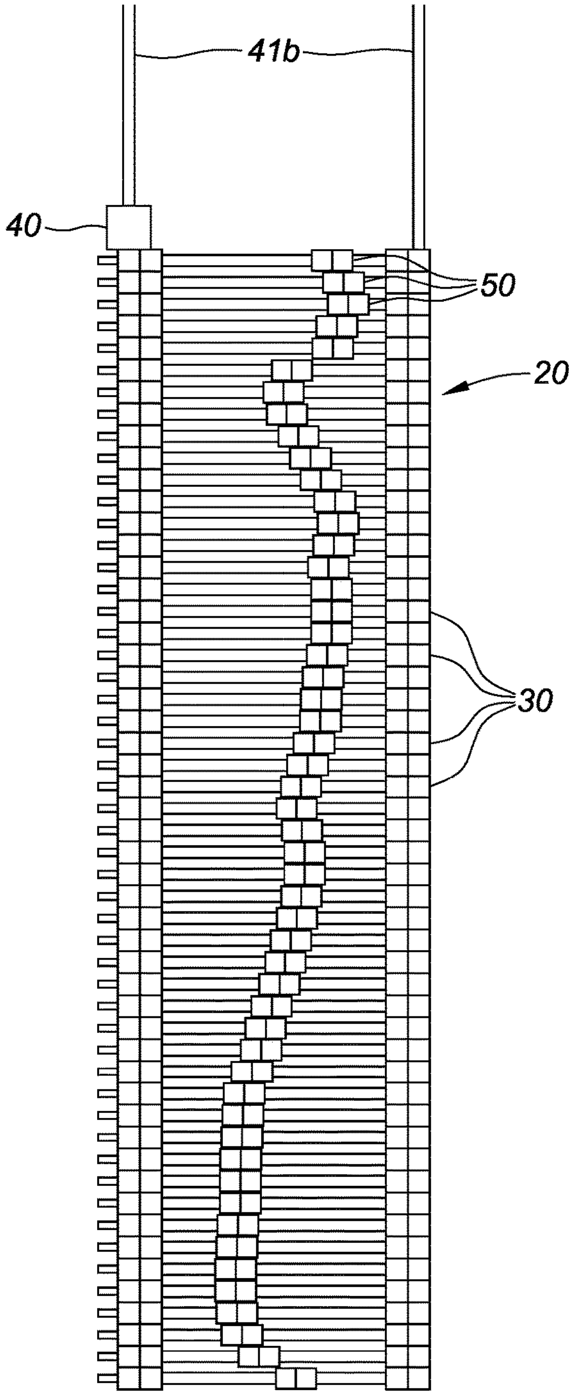
FIG. 4A is a schematic illustration showing a side view of an imaging stack of the camera of FIG. 1, arranged with a minimal spacing between imaging clusters, and with some pantograph arms removed to show underlying detail.
Figure 4B:
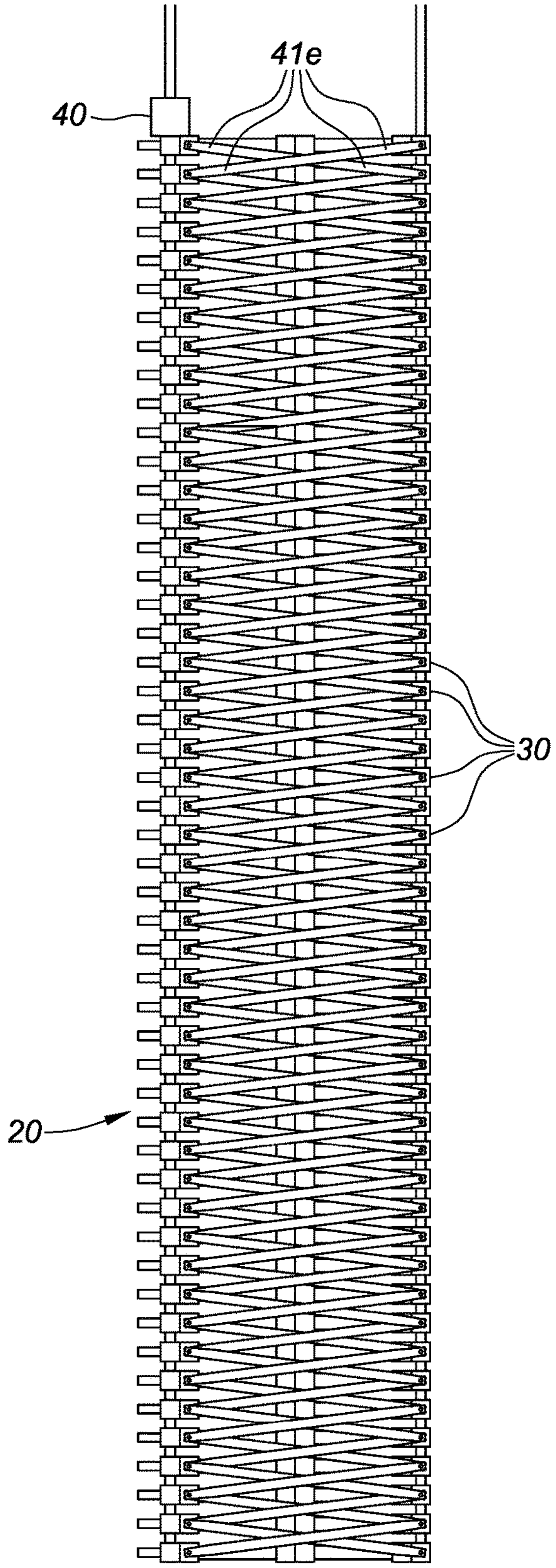
FIG. 4B is a schematic illustration showing a side view of an imaging stack of the camera of FIG. 1, similar to that of FIG. 4A, but arranged with a larger spacing between imaging clusters, and also illustrating pantograph arms.

The stack 20 can comprise a cluster spacing mechanism 32 with at least one a spacing linear motion screw 41*a* that is rotated by a spacing drive motor 41*c*, and a spacing pantograph mechanism 41*d* having pantograph arms 41*e* coupled to each of the imaging clusters 30. Rotation of the spacing linear motion screw 41*a* causes expansion of the stack 20 along the stack axis 22, while the spacing pantograph mechanism 41*d* maintains the distance between each adjacent imaging cluster 30 uniform, so that the imaging clusters 30 are equally spaced along the stack axis 22. The imaging clusters 30 follow along at least one spacing alignment guide 41*b* to maintain orientation of the imaging clusters 30 in alignment with each other along the stack axis 22. The spacing linear motion screw 41*a* can comprise a ball screw, although a lead screw, Acme screw, roller screw, threaded rod, or other linear actuator arrangements can be utilized to move the imaging clusters 30 to adjust for the particular body height 9 of the body 8 being imaged. The cluster spacing mechanism 32 can comprise a spacing linear motion screw 41*a* attached to the stack 20 near the top of the stack 20, and a spacing linear motion screw 41*a* attached to the stack 20 near the bottom of the stack 20, with each spacing linear motion screw 41*a* rotatable by a respective spacing drive motor 41*c*. A first one of the spacing linear motion screws 41*a* and respective spacing drive motor 41*c* can be attached to the bottom imaging cluster 30, and a second one of the spacing linear motion screws 41*a* and respective spacing drive motor 41*c* can be attached to the top imaging cluster 30. A series of pantograph arms 41*e* can be interconnected with each other and with each of the imaging clusters 30 in an accordion or scissor pantograph structure, so that the cluster spacing mechanism 32 maintains a similar spacing between each of the adjacent imaging clusters 30 in the stack 20, while allowing the vertical spacing between the imaging clusters 30 to all increase or decrease in concert. In alternate embodiments, each imaging cluster 30 includes a spacing drive motor 41*c* with associated gearing to adjust the spacing between each adjacent imaging cluster 30 independently. In one embodiment, each spacing drive motor 41*c* can be operated to obtain a uniform spacing between each adjacent imaging cluster 30. The varied spacing between imaging clusters 30 is further illustrated in FIGS. 4A and 4B. In FIG. 4A, stack 20 is arranged with minimal spacing between imaging clusters 30, such as to accommodate a small body 8 to be imaged. In FIG. 4A, some of the pantograph arms 41*e* have been removed to show the underlying structure, including the imaging sensors 50 that are arranged at different locations by the respective standoff positioning mechanisms 38, so that each imaging sensor 50 is at the desired standardized standoff distance 70 from the particular portion of the body 8 being imaged by the respective imaging sensor 50. In FIG. 4B, stack 20 is arranged with greater spacing between imaging clusters 30, such as to accommodate a larger body 8 to be imaged.

Figure 5:
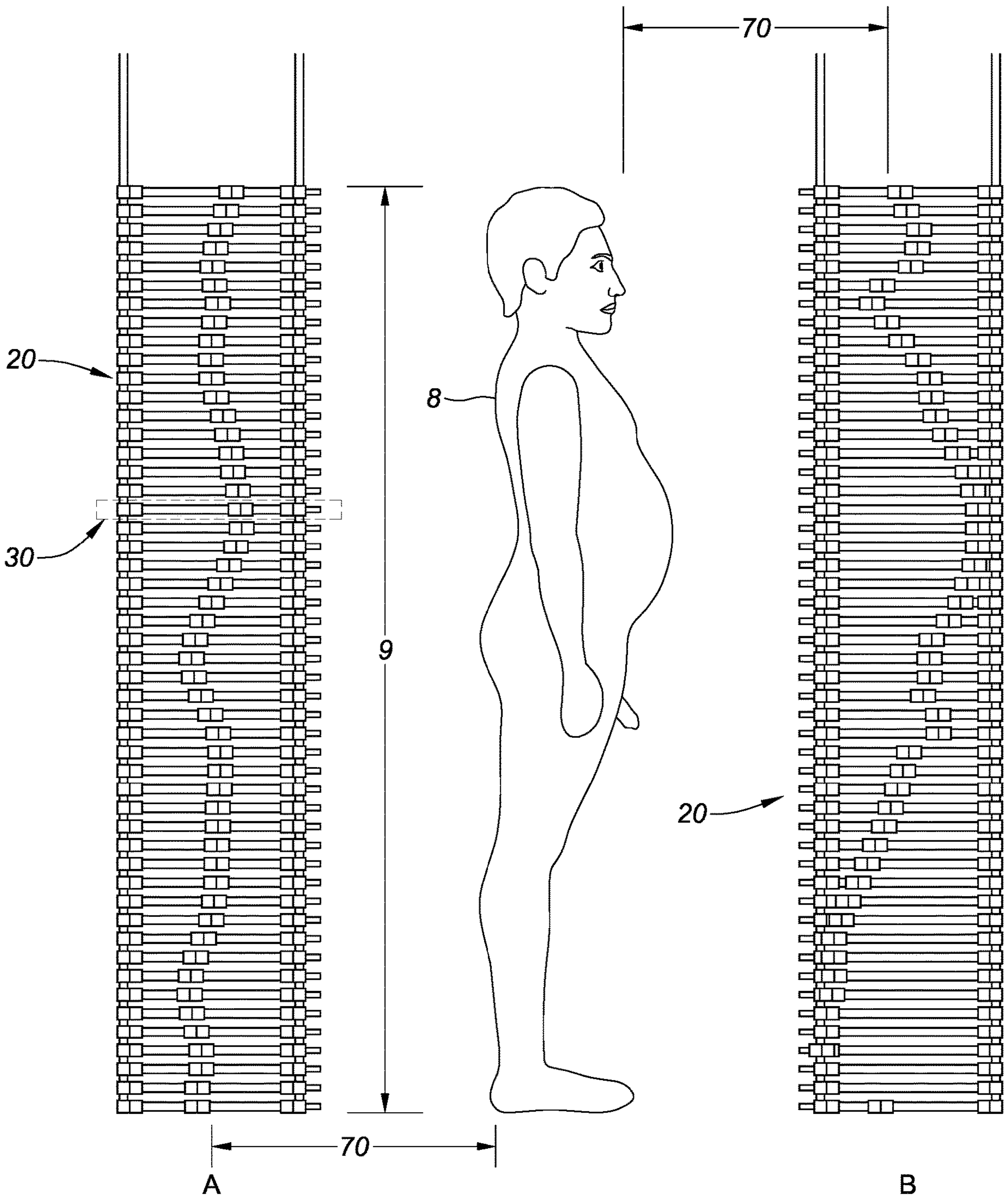
FIG. 5 is a schematic illustration showing a side view of an imaging stack arranged with each imaging sensor positioned at a predetermined standoff distance from a body, with view A illustrating a configuration wherein the imaging stack is arranged for imaging of the posterior aspect of the body, and with view B illustrating the configuration wherein the imaging stack has been rotated from the configuration of view A and is arranged for imaging of the anterior aspect of the body.

The stack 20 of imaging clusters 30 is coupled with a stack rotation mechanism 24 to rotate the stack 20 around a central axis 14 of the imaging chamber 12, which can be a cylindrical space around which the stack 20 of imaging clusters 30 can rotate to capture images around the full 360° circumference of the body 8. In some embodiments, the central axis 14 is approximately vertical, so that a patient could stand up within the imaging chamber 12. In other embodiments, the camera 10 is configured with the central axis 14 being approximately horizontal, so that a patient could lay on a horizontal support 16 within the imaging chamber. In one embodiment, the stack 20 includes at least 25 imaging clusters. In other embodiments, the stack 20 can comprise at least 50 imaging clusters, such as the examples illustrated in FIG. 4A-4B. In yet other embodiments, the stack 20 includes about 100 imaging clusters. In one embodiment, the height detector 40 and the cluster spacing mechanism 32 are used to adjust the spacing between the imaging clusters 30 so that the imaging clusters 30 are all aligned to orient the respective imaging sensors 50 along the entire extent of the body 8 but not beyond the body height 9 so that the maximum amount of image data is obtained. In one embodiment, as the stack 20 is rotated around the central axis 14 of the imaging chamber 12, the standoff positioning mechanism 38 is utilized to adjust the position of the imaging sensor 50 in each imaging cluster 30 to the predetermined standoff distance 70 from the particular portion of the body 8 being imaged by the respective imaging sensor. The stack 20 is illustrated in two example locations around the circumference of the body 8 in FIG. 5. View A of FIG. 5 illustrates the stack 20 (again with some pantograph arms 41*e* removed to illustrate underlying structure) with the imaging clusters 30 configured to locate each imaging sensor 50 at the desired standoff distance 70 from the particular portion of the body 8 being imaged by the respective imaging sensor 50; in in view A of FIG. 5, the stack 20 is oriented to image the posterior surface of the body 8. One of the imaging clusters 30 in the stack 20 is generally indicated by the dashed box in View A. View B of FIG. 5 illustrates the same stack 20 as in view A of FIG. 5, with the stack 20 having been rotated by the stack rotation mechanism 24, so that the anterior portion of the body 8 can be imaged, and the imaging sensors 50 have each been moved by the respective standoff positioning mechanism as necessary to locate each imaging sensor 50 at the desired standoff distance 70 from the particular portion of the body 8 being imaged by the respective imaging sensor 50. In a similar manner, the imaging sensors 50 are moved by the respective standoff positioning mechanism as necessary while the stack 20 is rotated around the central axis 14 to so that each imaging sensor 50 is at the desired standoff distance 70 from the particular portion of the body 8 being for each image capture by each imaging sensor 50. The stack 20 essentially "morphs" to the shape of the body 8 as the stack 20 rotates around the body 8, and takes on the varying profiles of the body, and thus the camera can be considered "anthropomorphic".

In some embodiments, each imaging cluster 30 in the stack 20 includes a standoff distance sensor 36, and measures the standoff distance 70 at each imaging cluster 30. A set of standoff distances 70 measured from multiple standoff distance sensors 36 can be considered an array of standoff distances, with the array of standoff distances used to adjust the position of each imaging cluster 30 in the stack 20. The entire set of standoff distances 70, correlated with the location of each of the particular imaging clusters 30, can be considered a volumetric point cloud representing the surface of the body 8. This volumetric point cloud data can be stored for correlation with the images 80, or for comparison with other volumetric point cloud data.

The imaging sensor 50 can comprise a slit-scan or rotating line sensor such as may be used in panoramic cameras, except in the present invention, the sensor 50 rotates around the body 8 rather than spinning to capture an external view. Alternatively, a digital imaging sensor with a fixed-focus lens of a fixed focal length can be utilized. In some embodiments, the imaging sensors 50 are sensitive to electromagnetic radiation in the visible spectrum. In some embodiments, the imaging sensors 50 are sensitive to electromagnetic radiation of one or more particular wavelengths within the visible spectrum. In some embodiments, the imaging sensors 50 are sensitive to ultraviolet or infrared radiation. In some embodiments, the imaging sensors 50 are sensitive to electromagnetic radiation of wavelengths that may include radiation in infrared, visible, and ultraviolet wavelengths or combinations or ranges thereof. The resolution of available imaging sensors is increasing over time, but the imaging sensor 50 is chosen so that the images obtained are of very high resolution. Currently, ultra-high-definition imaging sensors with about 3840 by 2160 pixels are available, and ultra-high-definition imaging sensors can provide effective imaging of the skin of the body 8 to capture images of skin structures comparable to the smallest skin structures that can be seen by the unaided human eye. The imaging sensor 50 is positioned by the standoff positioning mechanism 38 so that the small portion of the body 8 being imaged at a particular time by a particular imaging sensor 50 is in-focus, minimizing depth-of-field requirements, and obtaining a sharp focused image. The imaging sensor 50 can be configured and arranged at a focal length comparable to that of the human eye so that the resulting image is undistorted compared to what a human viewer would perceive. Each imaging cluster 30 in the stack 20 is simultaneously adjusted to the predetermined standoff distance 70, with some imaging sensors 50 moved inward towards the central axis 14 or outward away from the central axis 14 in order to locate all the imaging sensors at the predetermined standoff distance 70 to accommodate the irregular shape of the particular portions of the body 8 being imaged by each of the imaging sensors 50. The movement of each imaging cluster 30 is accomplished by driving the standoff linear motion screw 39*a* with the standoff drive motor 39*c* while the orientation of the imaging sensor 50 is maintained by the standoff alignment guide 39*b*. When each of the imaging sensors 50 are at the predetermined standoff distance 70, the imaging sensors 50 are each used to capture images at equal distance locations along the stack axis 22, each image being exposed at a standard exposure value and with the particular portions of the body 8 each being in focus. The stack 20 is rotated around the central axis 14 by the stack rotation mechanism 24, with each imaging sensor 50 directed inwardly toward the central axis 14 and the body 8. As the stack 20 is rotated around the central axis 14, each standoff distance sensor 36 is used to adjust the respective standoff positioning mechanism 38 to locate the respective imaging sensor 50 at the predetermined standoff distance 70 so that each particular portion of the body 8 is in focus, even with the body being irregularly shaped. The imaging sensors 50 can each be used to capture multiple focused images of the body 8 as the stack 20 is rotated around the central axis 14. In one embodiment, each imaging sensor 50 is used to capture multiple images at no more than about 10 degree increments around the central axis 14. In other embodiments, each imaging sensor can be used to capture multiple images at no more than 15 degree increments around the central axis. In yet other embodiments, each imaging sensor 50 can be used to capture images at increments less than about 2 degrees around the central axis 14. In yet other embodiments, each imaging sensor 50 is used to capture images at increments of about 1 degree around the central axis 14. In yet other embodiments, each imaging sensor 50 is used to capture images at increments of less than 1 degree around the central axis 14. For example, a stack of 50 imaging clusters 30, with imaging sensors 50 capturing 360 images in 1-degree increments around the central axis 14, would capture 18,000 images covering the surface of the body 8, with minimal distortion, in focus, and in a repeatable manner.

In one embodiment, the imaging sensor 50 passes digital image data to a data storage device 90 via data connection 92. The stored image data can then be manipulated by an image processor as needed for further analysis, or utilized for sequential comparisons at different times, such as to monitor changes in skin lesions over time. The stored image data can be utilized for monitoring changes over time, for comparing scanned individuals, for automated image analysis to detect particular locations of interest on the surface or skin of the body 8. In some embodiments, the stored image data can be utilized for creation of a map of skin features such as size, shape, coloration, texture, and surface projection, which can include highlighting of such specific skin features.

In some embodiments, slit scanning is used in order to create a single 360-degree inwardly-panoramic image capture from each imaging sensor 50, and the resulting in repeated manner until the body 8 has been imaged around 360 degrees. The multiple image captures from each imaging sensor 50 can then be digitally "stitched" together to create a complete 360-degree image of the skin of the body 8 along the entire body height 9, for example. In some embodiments the imaging sensors 50 capture multiple separate images around the body, and these multiple separate images from each of the imaging sensors 50 are digitally "stitched" together to create a complete 360-degree image of the skin of the body 8 along the entire body height 9, for example.

In one embodiment, the stack rotation mechanism 24 includes a lower turntable 60 with a central platform 62 that is stationary, so that a patient body 8 within the imaging chamber 12 is stationary, while the stack rotation mechanism 24 rotates the stack 20 around the central axis 14. In other embodiments, the stack 20 is not rotated, but the central platform 62 is rotated, with a similar set of standardized and focused images obtained by the plurality of imaging sensors 50 in the respective imaging clusters 30. The stack rotation mechanism 24 preferably includes an upper turntable 64. The stack 20 preferably includes a plurality of spacing alignment guides 41*b* that are secured to the lower turntable 60 and the upper turntable 64 to maintain vertical alignment of the plurality of imaging clusters 30 in the stack, even when the spacing between the imaging clusters 30 is adjusted with the cluster spacing mechanism 32. In some embodiments, the stack 20 can comprise 4 spacing alignment guides 41*b* along which the imaging clusters 30 follow.

In some embodiments, the stack rotation mechanism 24 is utilized to rotate the stack 20 in a circular arc less than 360 degrees. For example, the stack 20 can be rotated 180 degrees, or 90 degrees, or some other portion of a complete circumferential arc. This approach can be utilized to document and examine other objects, or only a particular portion of the body, as may be needed for a particular study, documentation, or diagnosis. Multiple partial images such as this may be combined, such as using the camera 10 to capture two 180-degree images that can be digitally "stitched" together if desired. In some embodiments, the camera 10 can include a plurality of stacks 20, with each stack configured to rotate in a circular arc less than 360 degrees, and images 80 from the imaging sensors 50 in each of the stacks 20 can be combined or digitally "stitched" together. For example, the camera can include 2 stacks 20, each capturing a 180-degree imaging range, or 4 stacks 20, each capturing a 90-degree imaging range, to combine and form complete imaging around 360 of the body 8. In some embodiments, the stack 20 is mounted on a carrier (not shown), and the stack rotation mechanism 24 moves the carrier(s) relative to the body 8.

Figure 6:
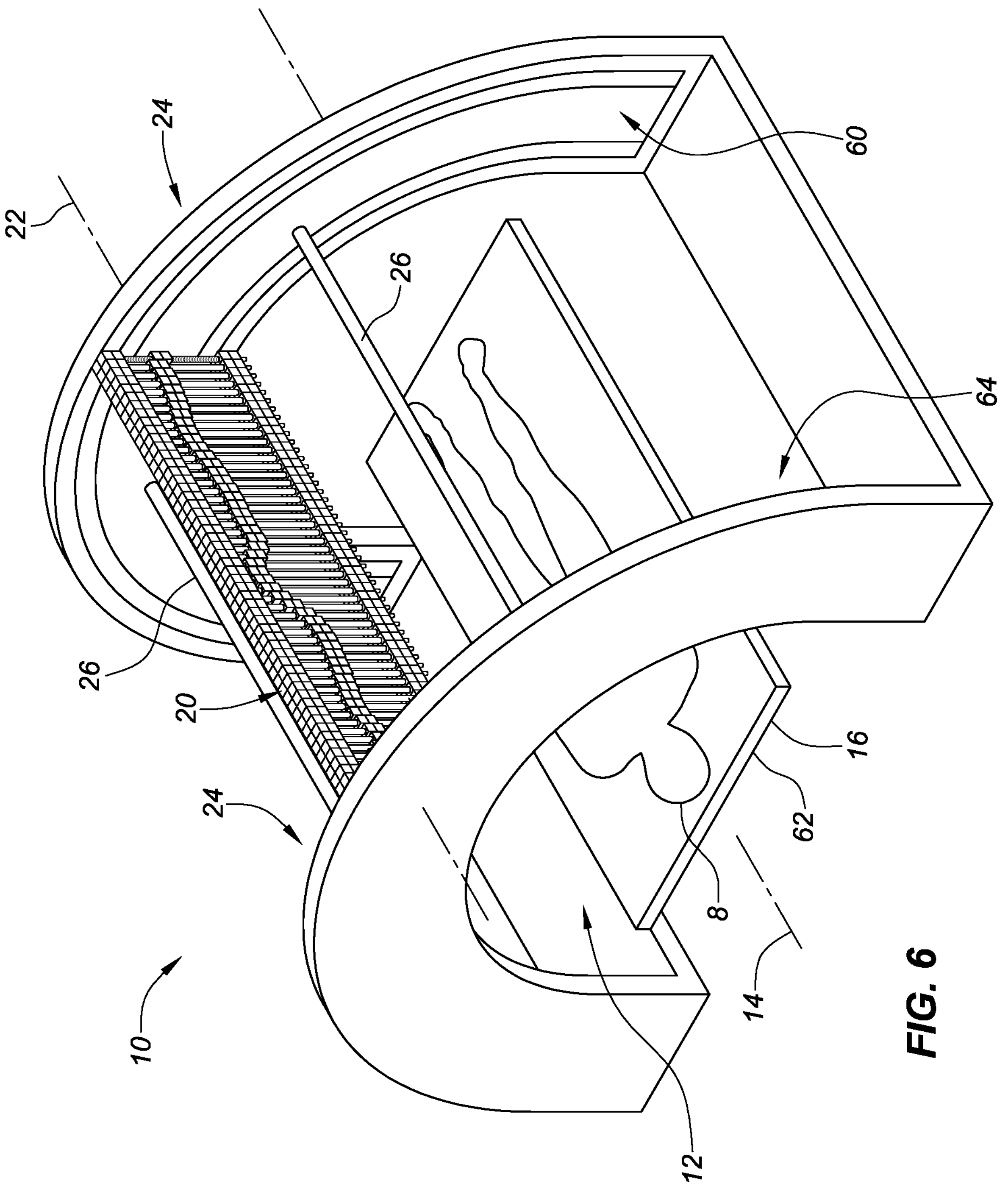
FIG. 6 is a schematic perspective illustration of a camera of the present invention, similar to the camera of FIG. 1, but arranged with a horizontal central axis, and with a target body resting on a horizontal support within an imaging chamber.

In some embodiments, the camera 10 can be arranged so that the central axis 14 and the stack axis 22 are approximately horizontal, and a patient or other object or body 8 to be imaged is placed on a horizontal support 16 within the imaging chamber. FIG. 6 is a schematic perspective illustration of the camera 10, configured with a horizontal central axis 14, and with a target body 8 resting on a horizontal support 16 within the imaging chamber 12. In this example, the stack 20 is secured to the upper turntable 64 and the lower turntable 60, but the central platform 62 is preferably in the form of a horizontal support 16. Lighting elements 26 can be located to provide ambient light onto the subject body 8 from 45 degrees on either side of the stack 20, and lighting elements 28 (not visible in the view of FIG. 6, but similar to that shown in FIG. 2) can be located to provide point light sources on proximate each imaging sensor 50, on opposed sides of the respective imaging sensor 50.

In some embodiments, the sensor 50 includes a sensor plate configured for mounting the sensor 50 in the imaging cluster 30. In some embodiments, each imaging cluster 30 may include lensing and sensors commonly associated with cameras, so that the stack 20 of imaging clusters 30 might be informally called an array of cameras. We consider the complete imaging device 10 as disclosed herein to be a single anthropomorphic camera.

Directional terms such as “height”, “top”, “bottom”, “side” and so forth generally are used herein with their ordinary meaning, consistent with the drawings herein illustrating the invention, but are not intended to be limiting. For example, while in many instances the stack 20 is oriented vertically, with the stack axis 22 being generally vertical, the stack 20 can be oriented in other orientations, such as horizontally, or at 15 degrees from vertical, or at other angles. In those situations, the directional terms such as “height”, “top”, “bottom”, “side” and so forth should be interpreted in similar manner with respect to the stack 20.

Early and accurate detection of skin cancers is an unsolved problem, with millions of skin tumors diagnosed each year, costing the healthcare system billions of dollars annually. Earlier detection would improve cure rates, minimizing patient deaths and surgical disfigurements. Unfortunately, skin cancer rates are increasing, and existing imaging devices lack the accurate and standardized rendering needed for effective diagnosis of skin anomalies or tracking of skin lesions over time, and have yet to show clinical benefit. No other skin imaging technique has yet shown clinical benefit. Primary care practitioners, dermatologists, and oncologists are constrained by the short amount of time that can be spent with any patient and insurance companies are reluctant to reimburse adequately for time-intensive, thorough skin-check examinations. The disclosed embodiments, systems, and methods allow for highly standardized skin surface documentation to image a three-dimensional skin surface or other three-dimensional body in a standardized and reproducible manner. Further, precise registration can be used to enable sequential imaging for identifying new lesions or detecting other changes over time to facilitate early detection of any small differences.

Rapid and reliable imaging of the skin is needed in order to efficiently detect and monitor skin anomalies, but existing devices and methods do not provide the standardized and registered skin imaging desired for comparison between scans or monitoring of changes over time. Unfortunately, no scientific study has shown that clinical outcomes improve with the use of any of the current, non-standardized skin imaging modalities.

Prior cameras generally capture images from light or other electromagnetic radiation reflected or radiated from a subject outside the camera, as focused by aperture or lens elements onto a sensor structure such as light-sensitive film or a digital imaging sensor. Typical still and video cameras capture images from a single perspective, outwardly-directed towards the subject. Panoramic cameras similarly capture images from outside the camera, but generally rotate to capture a larger field of view. The present invention arranges the camera around the subject, with the camera inwardly-directed towards the subject, and can capture images from a 360-degree range of perspectives around the subject. The present invention camera 10 morphs its form to each object or body 8 so that capture of anatomic data from any specific portion of the body 8 generally occurs with the same imaging clusters 30 within the stack 20, again improving standardization and facilitating future anatomic research and investigation.

The present invention camera 10 adjusts to the height of a human body 8 that is within the imaging chamber 12. Height adjustment can be accomplished with a spacing pantographic mechanism **41*d* including an array of scissoring X-shaped elements to expand and contract the stack 20. In one embodiment, height adjustments can be enabled by infrared or laser height detectors 40 that are utilized to regulate spacing drive motors 41*c* that can be located near the top and bottom of the stack 20 and rotate respective spacing linear motion screws 41*a* to move the pantographic mechanism 41*d* and expand or contract the stack 20 along the stack axis 22. In some embodiments, the stack 20 can be expanded or contracted to image most potential subject bodies 8** that are anticipated, such as from about 57 inches to about 86 inches. In other embodiments, the stack can be expanded or contracted to image bodies that are from about 10 to about 100 inches.

The imaging “surface” of the present camera 10 morphs to the exact shape of each body 8 being imaged, with each imaging sensor 50 adjusted to the same standoff distance 70 from the particular portion of the body 8 imaged by the respective imaging sensor 50, somewhat reminiscent of a profile gauge. As the stack 20 is rotated around the body 8 (or the body 8 is rotated within the imaging chamber 12, in some embodiments) each standoff positioning mechanism 38 adjusts the location of each imaging sensor 50 continuously so that further imaging is accomplished with each imaging sensor 50 at the same predetermined standoff distance 70, even though the body 8 may be irregular, with different dimensions and shapes at different locations around the central axis 14. Reflected light data is harvested circumferentially as the stack 20 continuously morphs corresponding to the external shape of each person while the stack 20 rotates and sweeps around the body 8. Said another way, imaging scans are made to the exact, unique, curvaceous shape of the body 8 in front of the sensors 50 at any given moment. This ensures that the image sensors 50 (and any associated lensing or other scanning elements) are always at a fixed focal distance from the skin (at or near the predetermined standoff distance 70), creating a faithful 3-dimensional visual record from nearly all possible perspectives around the body 8. Use of a fixed imaging distance, constant reproduction ratio, and rapid exposures ensures optimal and crisp focus over the entire body surface, standardization of anatomic size, and minimization of optical distortion. Data is harvested circumferentially for subsequent image-processing into a detailed and accurate 3-D avatar of each individual body 8 scanned. In some embodiments, dense hair on the body 8 can be shaved, or pendulous anatomic structures covering a portion of the surface of the body 8 can be temporarily moved out of the way, so that virtually complete imaging of the skin of the body 8 is obtained by the camera 10.

In one embodiment, the standoff positioning mechanism 38 and the cluster spacing mechanisms 32, as informed by the height detector 40 and the standoff distance sensors 36, operate to automatically adjust the spacing between the imaging clusters 30 prior to the start of the scan, and to automatically adjust the standoff distance as the stack 20 of imaging clusters 30 with imaging sensors 50 is rotated by the stack rotation mechanism 24 around the central axis 14 to image the surface of the body 8. Preferably, the entire body 8 is scanned in a single sweep, but smaller vertical segments can be imaged separately and subsequently assembled or digitally "stitched" together if desired.

In some embodiments, the camera 10 can be used to obtain standardized imaging of the skin of a human patient suitable for screening or diagnosis, avoiding the need for direct contact or visualization of the skin by a medical practitioner. Reducing or avoiding the need for such direct contact can reduce costs and improve safety, and may facilitate virtual examinations.

One object of the present invention is to provide standardized imaging of irregular or rounded objects such as the skin of a patient, with the entire surface in focus.

Another object of the invention is to provide standardized and reproducible imaging for detailed comparison between individuals with standardized lighting and perspective.

Yet another object of the invention is to provide standardized and reproducible imaging for repeated imaging over time for accurate observation and tracking of any changes overtime.

Still another object of the invention is minimizing perspective variations and distortions to provide standardized imaging of the external envelope of an irregular body.

A further object of the invention is to obtain images of an irregular body with minimal extrapolation.

A still further object of the invention is to efficiently obtain accurate and reproducible skin imaging to detect and track skin lesions over time.

A yet further object of the invention is to provide standardized imaging of nearly the entire skin surface of a body.

In some embodiments, the invention includes apparatus and methods for creating ultra-high-definition undistorted imaging for creating a three-dimensional anthropomorphic avatar including shape, color, size, texture, surface morphology, and volume at each level of the body.

Exemplary claims include the following:

1. A medical imaging device for creating a three-dimensional image of a body surface, the device comprising: a sensor array comprising a plurality of sensors, each sensor comprising a sensor plate, and each sensor configure to collect skin data regarding skin features and conditions; means for adjusting a standoff distance from the body surface to each sensor plate of each sensor in said sensor array, creating an array of standoff distances, wherein each standoff distance comprising said array of standoff distances may be unique from each other standoff distance comprising said array of standoff distances, and whereby said plurality of sensors are adapted to duplicate a shape of the body surface; means for adjusting a sensor vertical separation distance between adjacent sensors of said sensor array; means to facilitate movement of said sensors array around the body surface to capture images of the body surface from various angles while maintaining at least one target standoff distance and collecting spatially registered skin data; means for generating a volumetric point cloud representing the body surface; and means for storing said spatially registered skin data tied to said volumetric point cloud.
2. The medical device of claim 1, wherein said means for adjusting each standoff distance facilitates real-time adjustment as said array of sensors moves relative to the body surface, whereby a focal length of each sensor in said sensor array remains constant.
3. The medical device of claim 1 further comprising means for adjusting lighting.
4. The medical device of claim 3, wherein each sensor in said plurality of sensors is adapted to collect said skin data using visible light.
5. The medical device of claim 1, wherein each sensor vertical separation distance may be unique.
6. The medical device of claim 1, wherein each said sensor plate comprises sensor-guided sensor plates configured to harvest reflected visible light from a fixed distance orthogonal to the body surface.
7. The medical imaging device of claim 1, wherein each sensor further comprises a slit lens for scanning of the body surface; said means for adjusting a standoff distance further comprises horizontal sensor glide bars, supports for said horizontal sensor glide bars, threaded rods for horizontal sensor movement, ball screw motors for horizontal sensor movement, and structural supports for said horizontal glide bars; and said means for adjusting a sensor vertical separation distance further comprises vertical sensor-separation glide bars, supports for vertical movement on said sensor-separation glide bars, a pantograph vertical expansion element, a ball screw motor for said pantograph vertical expansion element, and a threaded rod for pantographic vertical expansion.

It is to be understood that even though numerous characteristics and advantages of the present invention have been set forth in the foregoing description, together with details of the structure and function of the invention, the disclosure is illustrative only, and changes may be made in detail, especially in matters of shape, size, number, and arrangement of parts within the principles of the invention to the full extent indicated by the broad general meaning of the terms in which the appended claims are expressed. Specific elements herein described with relation to any of the embodiments disclosed herein may be combined or substituted to the extent that such combination or substitution is consistent with the general functioning of the invention and the teachings herein, and as consistent with the appended claims.

What is claimed is:

1. A medical imaging device for creating a three-dimensional image of a body surface, the device comprising:

a sensor array comprising a plurality of sensors, each sensor comprising a sensor plate, and each sensor configured to collect skin data regarding skin features and conditions;

a standoff positioning mechanism for adjusting a standoff distance from the body surface to each sensor plate of each sensor in said sensor array, creating an array of standoff positions, each standoff position comprising a horizontal position of the sensor within the sensor array, wherein each standoff position comprising said array of standoff positions may be unique from each other standoff position comprising said array of standoff positions, and whereby said sensor array is adapted to duplicate a shape of the body surface based on the array of standoff positions a cluster spacing mechanism for adjusting a sensor vertical separation distance between adjacent sensors of said sensor array;

a stack rotation mechanism to facilitate movement of said sensors array around the body surface to capture images of the body surface from various angles while the standoff positioning mechanism maintains at least one target standoff distance and the sensor array collects spatially registered skin data;

wherein said array of standoff positions, correlated with a location of each sensor in said sensor array, comprises a volumetric point cloud representing the body surface; and a data storage device for storing said spatially registered skin data tied to said volumetric point cloud.

2. The medical device of claim 1, wherein said standoff positioning mechanism for adjusting each standoff distance facilitates real-time adjustment of each standoff position as said array of sensors moves relative to the body surface, whereby a focal length of each sensor in said sensor array remains constant and whereby the standoff positioning mechanism maintains the standoff distance for each sensor as the array of sensors moves relative to the body surface.

3. The medical device of claim 1 further comprising:

controllable lighting elements for adjusting lighting.

4. The medical device of claim 3, wherein each sensor in said plurality of sensors is adapted to collect said skin data using visible light.

5. The medical device of claim 1, wherein each sensor vertical separation distance may be unique.

6. The medical device of claim 1, wherein each said sensor plate comprises laser-guided sensor plates configured to harvest reflected visible light from a fixed distance orthogonal to the body surface.

7. The medical imaging device of claim 1, wherein:

each sensor further comprises a slit lens for scanning of the body surface;

said standoff positioning mechanism for adjusting a standoff distance further comprises horizontal sensor glide bars, supports for said horizontal sensor glide bars, threaded rods for horizontal sensor movement, ball screw motors for horizontal sensor movement, and structural supports for said horizontal glide bars; and said cluster spacing mechanism for adjusting a sensor vertical separation distance further comprises vertical sensor-separation glide bars, supports for vertical movement on said sensor-separation glide bars, a pantograph vertical expansion element, a ball screw motor for said pantograph vertical expansion element, and a threaded rod for pantographic vertical expansion.

* * * * *